United States Patent [19]

Li

[11] Patent Number: 5,587,925

[45] Date of Patent: Dec. 24, 1996

[54] FILE TESTING TECHNIQUES

[75] Inventor: Cheng J. Li, Leominster, Mass.

[73] Assignee: Simonds Industries, Inc., Fitchburg, Mass.

[21] Appl. No.: 336,188

[22] Filed: Nov. 8, 1994

[51] Int. Cl.$^6$ ............................................. G01M 13/00
[52] U.S. Cl. ............... 364/508; 364/551.01; 364/474.06; 364/474.17
[58] Field of Search ........................ 364/508, 551.01, 364/472, 474.06, 474.17, 474.19; 73/7, 104; 29/76.1, 407; 409/244, 293, 131; 451/21, 419; 76/12

[56] References Cited

U.S. PATENT DOCUMENTS

| | | | |
|---|---|---|---|
| 4,120,196 | 10/1978 | Hamilton et al. | 73/104 |
| 4,694,686 | 9/1987 | Fildes et al. | 73/104 |
| 5,251,144 | 10/1993 | Ramamurthi | 364/474.19 |

OTHER PUBLICATIONS

Description of the Old File–Testing Machine along with Figures 1.1–4.1; May 30, 1995; 5 pages.
U. S. Government Services Agency, Federal Specification on File, Hand (American Pattern) and Rasp, Hand, GGG–F–3256, Oct. 31, 1966, pp. 1–27.
U.S. Government Services Agency, Commercial Item Description File, Hand (American Pattern), Half–Round, A–A–2312, Sep. 27, 1985, pp. 1, 2.
U.S. Government Services Agency, Commercial Item Description File, Hand (American Pattern), Regular AA–2313, Sep. 27, 1985, pp. 1, 2.

*Primary Examiner*—Ellis B. Ramirez
*Assistant Examiner*—Hal D. Wachsman
*Attorney, Agent, or Firm*—Peter J. Manus

[57] ABSTRACT

A method of testing the characteristics of a file by providing a curve of the amount of material removed from a test bar as a function of the effective stroke area over which the file has been moved, the slope at a specified value of material that has been removed representing the cutting efficiency of the file and the value of the effective stroke area at such specified value representing the useful life of the file. Further, curves of the minimum filing forces needed to move the file for a selected stroke distance at selected compressive forces and of the maximum compressive forces which will not prevent a filing operation at selected filing forces can be used to determine the sharpness of a file relative to other files that have been similarly tested.

8 Claims, 5 Drawing Sheets

FILE TESTING TECHNIQUES

This invention relates generally to techniques for testing product characteristics and, more particularly, to techniques for testing the characteristics of files.

BACKGROUND OF THE INVENTION

It is desirable to test files at the point of manufacture, for example, in order to avoid the sale and delivery of files having characteristics which are unacceptable for their intended operation, or to test them subsequently at the point of use in order to determine if previously acceptable characteristics thereof have been retained over a period of time. Further, it is often desirable to retain an historical record of the characteristics of files for future reference as, for example, to compare a particular file's characteristics over time or to provide information for a statistical analysis of the characteristics of a large number of different files for future design reference purposes.

Test procedures have been described in the literature, as in "Federal Specification on File, Hand (American Pattern) and Rasp, Hand", published on Oct. 31, 1966, by the U.S. Government Services Agency, and identified by Document GGG-F-325b. Such test procedures basically involve checking a file manually on its tang hardness, hardness crack, warpage, and the uniformity of cutting. The performance of the file is determined using machine-cutting tests, as described therein. Additional acceptance testing criteria for American pattern files are also described in the government document FPNTP-A6-19428-A-8-22-72, published in 1972.

Key points relating to the above machine tests can be summarized as follows. The test bar is 1 inch square, AISI 4140 steel (uniformed hardened to Rc 35 ±2), and is "run-in" using a file of the same type, but not the file test samples, so that the surface of the test bar matches the contour of the test file. A load (i.e., a compressive force between the test bar and the file) is selected as 20, 25, or 30 pounds depending on the size, shape, and type of the file. A stroke rate of 50–65 strokes per minute with 5½" of maximum stroke is used. The file lifts clear of the test bar on its return stroke. The purpose of the test is to obtain a measurement of the gram removal over 1000 or 2000 strokes and to calculate the average gram removal based on the test results of 12 sample files.

A later Federal Specification, identified as A-A-2312, was issued to supplement Document GGG-F-325 on Sep. 27, 1985 but discussed nothing new with respect to the machine-cutting tests portion of the previous documents, apparently because there exist so many shapes and sizes of files, that no easy common procedures have been devised to effectively describe the performance of so many different files.

During use in various applications, a file is expected to be sharp, to be able to remove material rapidly (often referred to as having a high cutting efficiency), and to last a relatively long time (i.e., to have high durability). Cutting efficiency is a function of the file's tooth design, construction, and pattern. Durability of a file is indicated by the total area it files throughout its working life and is an important factor since it determines the total work a file is capable of doing. Sharpness, indicated by well-shaped teeth, establishes the degree of effortlessness involved in performing a filing motion, i.e., ability to use the least amount of work to make a specified cut. Overall a file should be such that it can not only do more work in less time with less effort, but also it can do it better. The major concerns of most industrial file users are the "grams removal rate" (in effect, the cutting efficiency), which is defined as the total grams of material that can be filed away (removed) using a selected number of strokes, and total useful life of the file. In contrast many, if not most, domestic consumer users appear to be more concerned about the feeling of the file's sharpness during use.

It is desirable to provide better tool and testing procedures which significantly improve the ability to establish suitable and meaningful criteria for a file's operating characteristics, as well as to determine such characteristics for particular files for comparison with such criteria. Such tool and testing procedures would permit a more accurate prediction of the file's potential adequacy of performance during use so that files not satisfying such criteria can be suitably detected and the file either reworked or rejected before sale and delivery to a customer or so that the performance of files already in use can be periodically rechecked.

BRIEF SUMMARY OF THE INVENTION

In accordance with the invention a testing technique has been devised for more accurately testing files in a manner which provides better information as to a file's performance characteristics and, hence, its acceptability for initial or continued use, which can be used to provide an historical record of such performance characteristics. Characteristic curves are generated which can be appropriately interpreted to describe the cutting efficiency, the predictable life, and the sharpness of a file. Thus, techniques are devised for determining the cutting efficiency of a file in terms of a particular characteristic curve which depicts the amount (usually expressed in grams) of material removed by a file as a function of the stroke area (usually expressed in square inches), that is, the area over which the file has moved during its strokes. The slope of such characteristic curve can be used to represent the efficiency of the file, while the stroke area required to remove a selected amount of removed material can be used to represent the effective life of the file, i.e., to reflect the file's durability. The sharpness of a file can be determined in terms of a characteristic curve of the minimum filing force, i.e., the minimum force needed to move a file forward for a selected distance over a bar of material to be filed at several selected levels of a compressive force, i.e., the downward force between the file and the bar of material to be filed. The sharpness can be alternatively determined in terms of a characteristic curve of the maximum compressive force, i.e., the maximum force which will not prevent a filing operation as a function of several levels of the filing force, which technique also provides an indication of the file's sharpness.

DESCRIPTION OF THE INVENTION

The invention can be described in more detail with the help of the accompanying drawings wherein.

Figure 1:
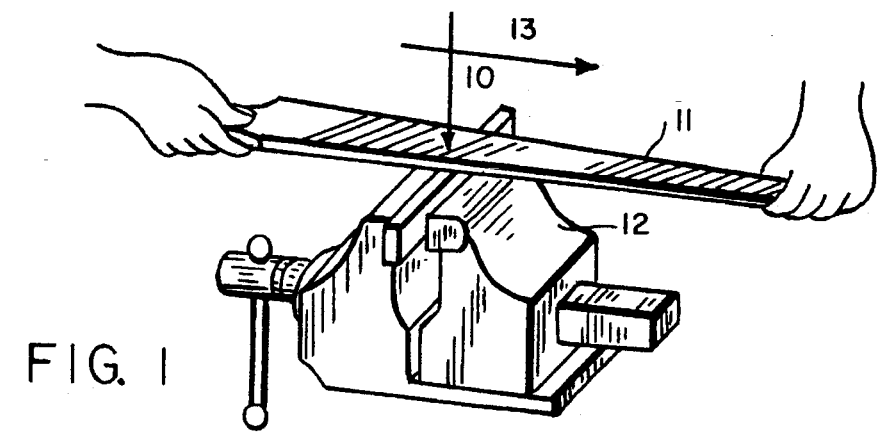
FIG. 1 shows diagrammatically the forces involved in a filing action.

As can be seen in FIG. 1, there are certain forces involved in a filing action which forces can be shown as essentially comprising two force vector components. For convenience, the figure demonstrates such forces as present, for example, in a manual filing operation. One component is a downward force shown by arrow 10 (i.e., a compressive force) which allows a file 11 to bite into the surface of the block or bar 12 of material which is to be filed. Another component is a forward force (i.e., a filing force) shown by arrow 13 which allows the file to move across a surface of bar 12 and carry away material from the surface. The compressive force is maintained at a selected value when a filing force of a selected value is applied (i.e., in an active filing stroke). At the end of a filing stroke the file is returned to its original filing position. There is no contact between the file and the surface of the bar during such return stroke (i.e., the idle stroke).

Figure 2:
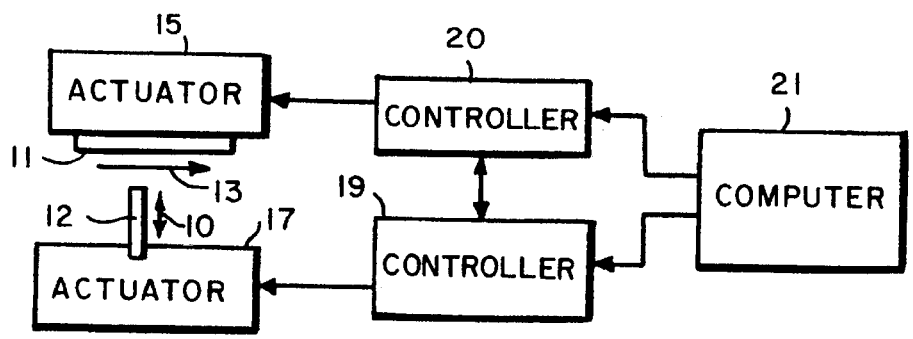
FIG. 2 shows a block diagram of an embodiment of a testing system which can use the procedures of the invention.

In accordance therewith, a suitable file testing machine can be constructed to simulate such a filing motion. As shown in FIG. 2, a first linear actuator 15, carrying a file 11, is mounted on a suitable, movable frame (not shown) and provides a filing force 13 (as in FIG. 1) in the direction shown. A second linear actuator 17, carrying a test bar 12 of material to be filed and moving at another motion profile, is movable vertically upwardly against the file to provide a compressive force 10 (as in FIG. 1) in a direction perpendicular to the filing force 13. The thrust force provided by actuator 17 is controlled by a controller 19 to provide the compressive force 10 between the file and the test bar. The thrust force provided by actuator 15 is controlled by a controller 20 to produce the filing force 13. The two controllers are linked to each other and to a computer 28 (e.g., a personal computer) so as to have interactive communication among such components. The velocity profiles provided by the two actuators are suitably programmed by the computer so as to simulate an actual filing motion. The computer 21 for allows for operator interaction, data acquisition, data manipulation, and report generation, as discussed more fully below.

Three characteristic curves are generated, one to describe the cutting efficiency of a file and to define the expected useful life of a file, and the others to express in at least two ways the sharpness characteristic of a file. Such curves include a first curve effectively showing grams removal, i.e., the amount of material removed from the test bar, as a function of the file stroke area, such curve being used to determine both the cutting efficiency and the useful life of the file; a second curve showing the minimum filing force needed to move the file over a selected stroke area as a function of various selected constant compressive forces between the file and the test bar; and a third curve showing the maximum compressive force which can be applied and still allow the file to move over a selected stroke area as a function of several selected constant filing forces on the file. The latter two curves can each be used to determine the file's sharpness characteristic.

The first aspect of a file's characteristic to consider is its grams removal rate. Instead of using a single value for such characteristic, i.e., the total amount in grams of material removed after a specified number of filing strokes, a characteristic curve of the grams removed vs. file stroke area is used. During a test run, the grams removal is measured indirectly by calculating it from the height reduction of the filed surface of the test bar. Thus, grams removal is calculated by using the following formula:

$$\text{Grams removal} = (\text{Cross-section of test bar}) \times (\text{Height reduction of test bar}) \times (\text{Density of test bar}) \quad (1)$$

In a specific example, the density of a test bar made of Micarta material is 24.0909 $g/in^3$. If a test bar having a test cross-section area of one inch square is used, the grams removal, for a file having a width which is greater than the cross-section area, is the product: $(1"\times 1") \times$(height reduction in inches)$\times 24.0909$ $g/in^3$. For a file width of less than the cross-section area, the initial term is the product of the file width and a unit cross-section area. The file stroke area is defined as the total effective area which is in contact with the file at the test bar surface. The total stroke area generally represents how long the file has been in service and is calculated by using the follow formula:

$$\text{Stroke area} = (\text{Smaller value of the file width or the test bar width}) \times (\text{Stroke length}) \times (\text{number of strokes}) \quad (2)$$

A procedure for obtaining a characteristic curve of grams removal vs. stroke area is set forth as follows:

1. Mount the file on actuator 15.
2. Mount the test bar on actuator 17.
3. Input information identifying the file under test to the computer.
4. Input to the computer the following test parameters: the desired values of a preset compressive force and a preset filing force to be used, a preset velocity profile of the file, a preset stroke length for the file, and a preset total stroke number.
5. The computer supplies these values as control codes to actuator controllers 19 and 20.
6. Move actuators 15 and 17 to their initial stroke positions.
7. Actuate actuator 17 to move the test bar upward until it presses against the file and maintain the preset compressive force.
8. Record the position of actuator 17 (i.e., the height of the test bar).
9. Actuate actuator 15 to move the file forward at the preset velocity profile, stroke length, and filing force, while maintaining the preset compressive force.
10. Actuate actuator 17 to move away from actuator 15 at the end-of-stroke position of actuator 15.
11. Return actuator 15 to its initial position.
12. Actuate actuator 17 to move upward until the test bar presses against the file and maintains the preset compressive force.
13. Record the position of actuator 17 (i.e., the height of the test bar surface) which is used to derive Y, where Y is the grams removed in the file stroke.
14. Repeat steps 9 to step 13 a selected number of times $X_t$, where $X_t$ is the selected file stroke area to be used.
15. Return actuators 15 and 17 to their initial positions.
16. Print out a report containing the file identification information, the test parameters, the data for, and a curve of, the grams removal as a function of stroke area, the file efficiency, and the predicted life of the file.

Figure 4:
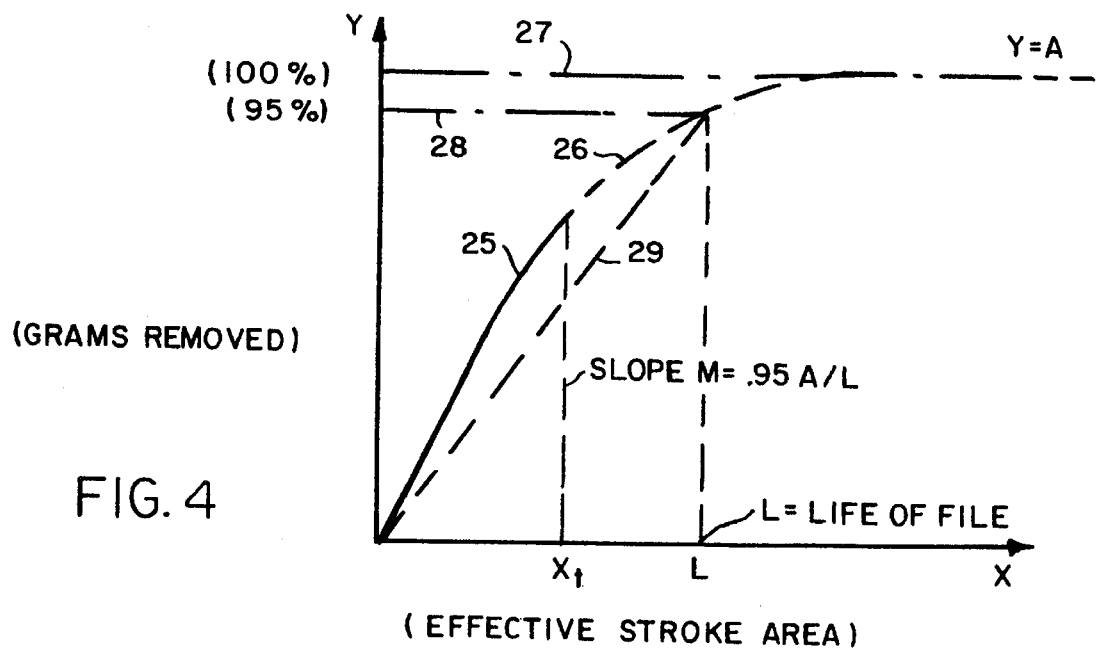
FIG. 4 shows an exemplary curve of effective grams removal as a function of effective stroke area obtained using the process of FIG. 3.
Figure 3:
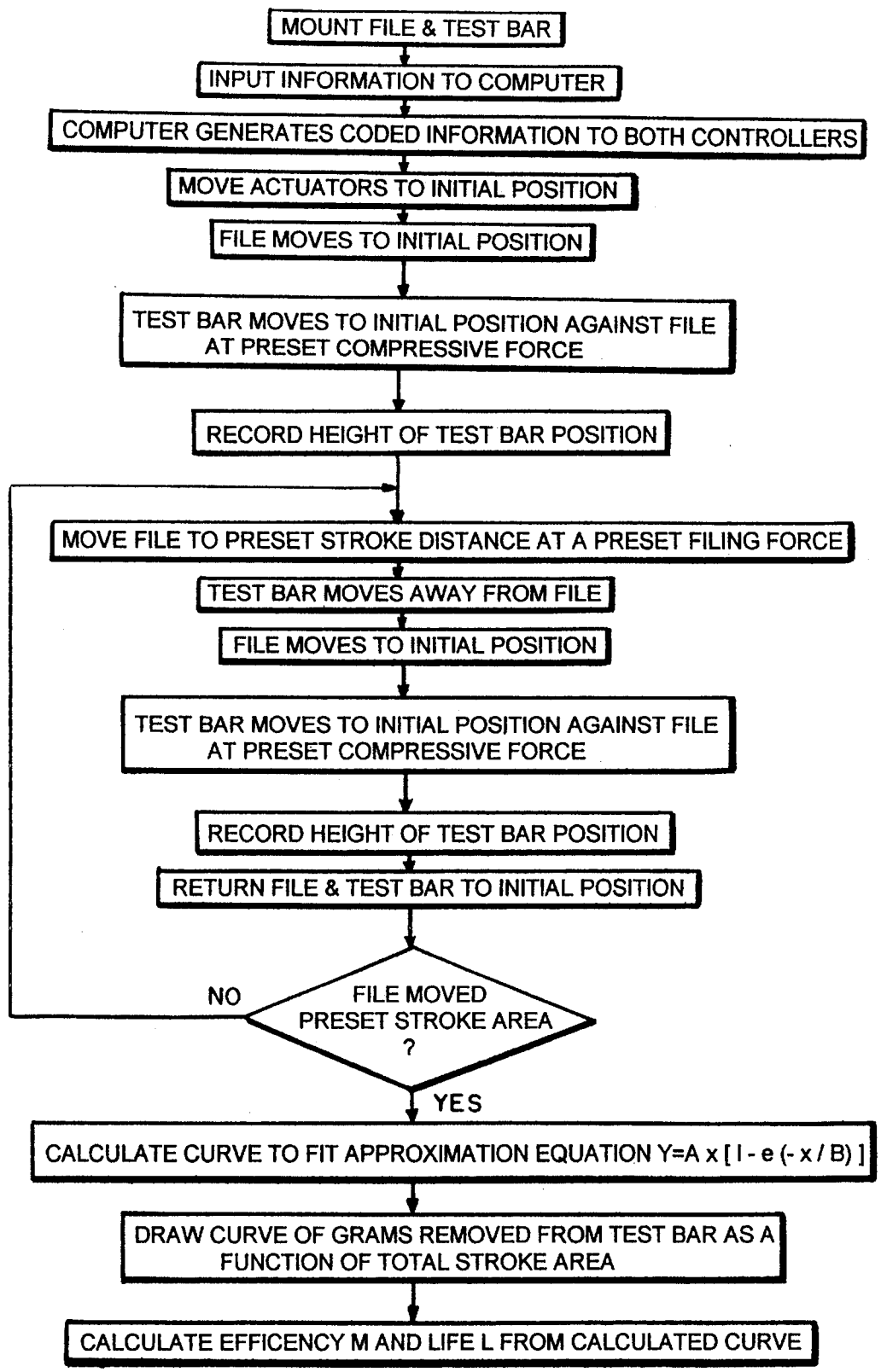
FIG. 3 shows a flow chart for implementing a test procedure for attaining a characteristic curve of grams removal as a function of stroke area.

Thus, the computer 21 can be programmed to perform the above procedure using a program devised in accordance with the flow chart shown in FIG. 3, which programming would be well within the skill of those in the art from such flow chart. The computer can be further programmed to generate a curve of grams removed Y as a function of stroke area X, up to $X_l$, obtained using the above procedure. Such a curve is depicted in FIG. 4 as solid line curve portion 25. The computer is further programmed to make use of such curve to produce a further curve portion, depicted by dashed line curve portion 26, so that an overall curve formed by curve portions 25 and 26 fits approximately a curve having the following approximation equation:

$$Y = A \times [1 - e^{(-X/B)}] \quad (3)$$

where A and B are constants, Y is the grams removed, and X is the effective stroke area, as defined above.

Physically the above equation represents a file which is gradually wearing out as the stroke area X increases, which file then has a deteriorating cutting ability. The constant A represents the upper limit of grams removal, i.e., the value of Y at an asymptote line 27 drawn to the overall curve maximum level in FIG. 4 and the value of B can then be appropriately computed. The cutting efficiency becomes very small at the end of curve (i.e., at the higher stroke area). A total stroke area L (i.e., where X=L) at which the grams of test bar material is removed to a selected fraction 28 of the upper limit A, e.g. 95% thereof in the example shown, can be defined as the useful life of the file. The slope M of the straight line curve 29 in FIG. 4, at the 95% point on the curve, represents the average grams removal rate over the effective life L of the file in units of grams removed per unit stroke area, and is used to provide a measure of the cutting efficiency of the file. Thus, such slope can be expressed as:

$$M = 95\% \times A/L \quad (4)$$

The programming of computer 21 to specifically implement the operation shown in the flow chart of FIG. 3, the generation of the overall curve shown in FIG. 4, the determination of the approximation curve and the constants A and B, and the computation of the life L and the slope M (efficiency) would be well within the skill of the art from the above description, and need not be described in further detail.

Figure 5:
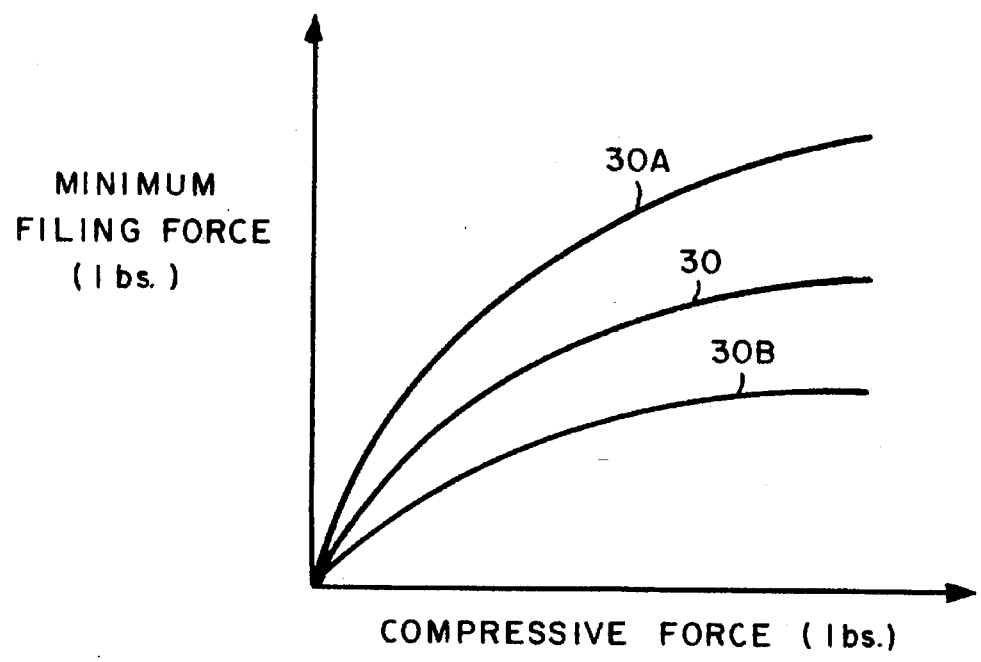
FIG. 5 shows an exemplary characteristic curve of minimum filing forces as a function of compressive forces.

Sharpness, which was formerly described in the art only qualitatively, can now also be effectively quantified by determining, first of all, the minimum filing force needed to move a file forward under a selected constant compressive force. If such minimum filing force is tested over a useful range of compressive forces, a characteristic curve of minimum filing forces as a function of compressive forces can be generated, as shown in FIG. 5.

The procedure for determining a characteristic curve of sharpness in such a manner is set forth as follows:

1. Mount the file on actuator 15.
2. Mount the test bar on actuator 17.
3. Input identification of the file to the computer.
4. Input the same test parameters as described above, except for a selected filing force.
5. Move actuators 15 and 17 to their initial positions.
6. Set a first selected filing force for the actuator 15, e.g., 10 lbs.
7. Supply the selected compressive force and the first selected filing force to actuator controllers 19 and 20, respectively.
8. Move actuator 17 forward until the test bar presses against the file and maintains the preset compressive force.
9. Move actuator 15 forward, at the preset first filing force, while maintaining the preset compressive force.
10. Move actuator 17 away from the actuator 15 at the end-of-stroke position of second actuator 15.
11. Record the distance actuator 15 has traveled.
12. If actuator 15 has not traveled the specified total stroke length, increase the filing force by specified amounts up to a selected amount, e.g., by 5 lbs. up to 15 lbs., and repeat step 5 to step 11, until actuator has traveled the specified selected stroke length.
13. Record the filing force needed in Step 12.
14. When actuator 17 has traveled the specified total stroke length, return actuators 15 and 17 to their initial positions.
15. Repeat steps 6 through 14 for several selected preset compressive forces.

Figure 6:
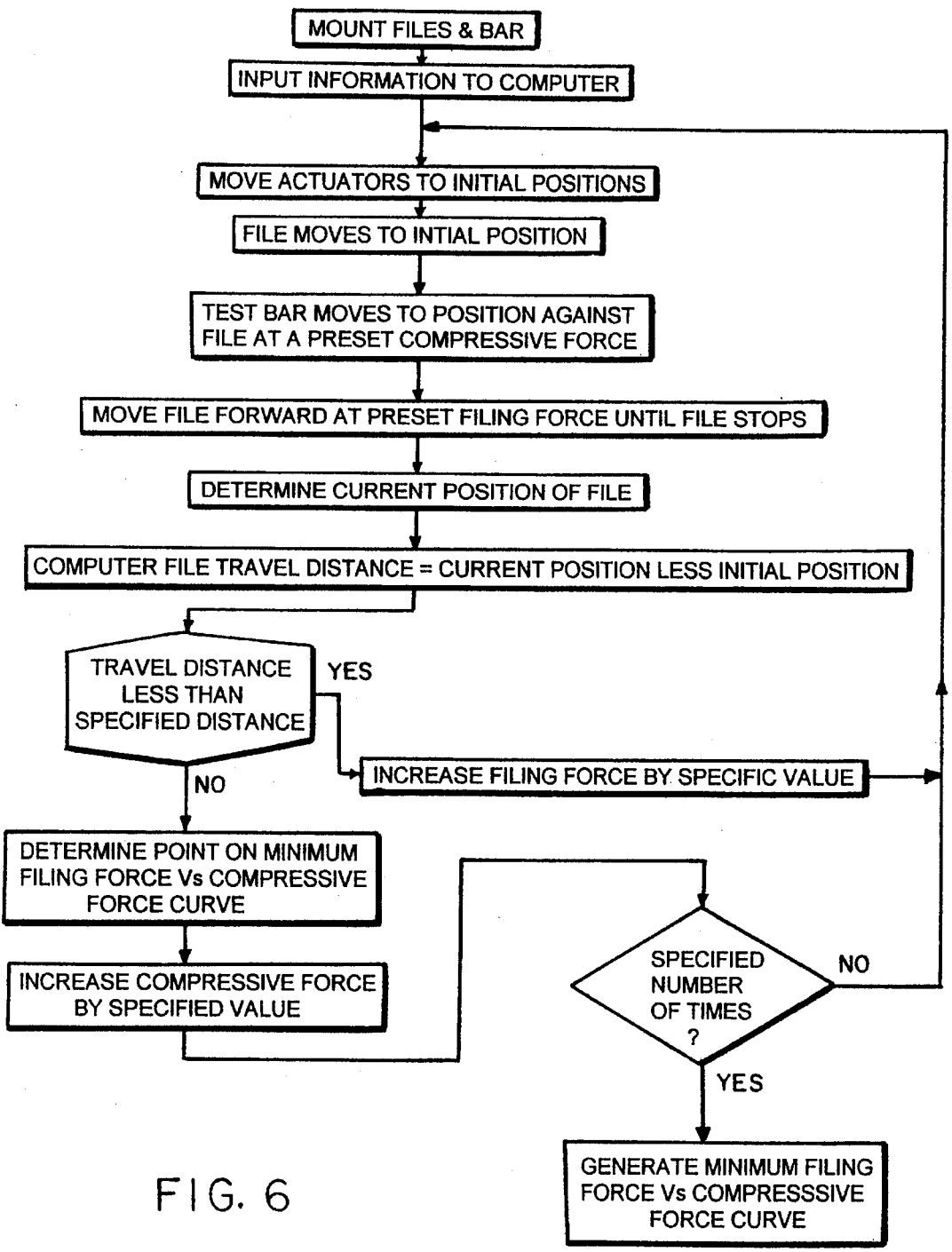
FIG. 6 shows a flow chart for implementing a test procedure to obtain a curve as depicted in FIG. 5.

Computer 21 can be programmed to implement such procedure in accordance with the flow chart depicted in FIG. 6. The computer can then generate a curve 30, such as shown in FIG. 5, from the determination of each successive minimum filing force needed at each preset compressive force. Such curve can be used as an indication of the sharpness characteristic of a file. Thus, if a file has a high sharpness, the curve 30 will be positioned relatively high on the graph of FIG. 5. For example, if a curve 30A above curve 30 is generated for a particular file, its sharpness will be indicated as relatively high as compared to that of a file having a curve 30, while a curve 30B below curve 30 indicates a low sharpness relative to curve 30. Thus, while an absolute measurement of sharpness is not determined, the sharpness of a file can be compared relatively to the sharpness of other files for which similar curves can be quantitatively generated so that over the course of testing a large number of different files an indication of the relative sharpness of each can be so determined.

Figure 7:
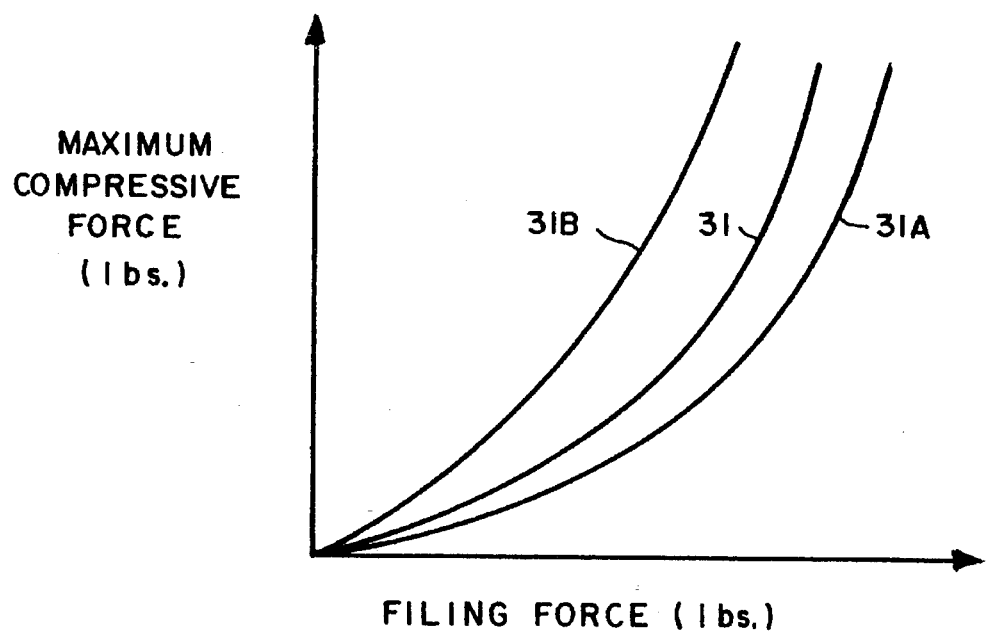
FIG. 7 shows an exemplary characteristic curve of maximum compressive forces as a function of filing forces.

An alternative process for determining the sharpness of a file quantitatively is to measure the maximum compressive three allowed that will not prevent a file from moving a specified total stroke distance when using a preset filing force. A characteristic curve of the maximum compressive force vs. filing force can be provided by repeating measurements over a useful range of filing forces, as shown in FIG. 7.

A procedure for determining this characteristic curve of sharpness in this measure is set forth as follows:

1. Mount the file on actuator 15.
2. Mount the test bar on actuator 17.
3. Input identification of the file to the computer.
4. Specify the test parameters as described above and a preset selected filing force.
5. Move actuators 15 and 17 to their initial positions.
6. Select a compressive force of actuator 17, e.g. 10 lbs.
7. Supply the selected compressive force and the preset filing force to actuators 19 and 20, respectively.
8. Move actuator 17 forward until the test bar presses against the file and maintains the selected compressive force.
9. Move actuator 15 forward at the preset filing force, while maintaining the selected compressive force.
10. Move actuator 17 away from actuator 15.
11. Determine the distance actuator 15 has traveled.
12. If actuator 15 has traveled a specified selected stroke length, increase the compressive force, by specified amounts, e.g., by 5 lbs up to 15 lbs., and repeat step 5 to step 11 until actuator 15 moves less than the specified selected stroke length.

13. When actuator 15 has traveled less than the specified selected stroke length, return actuators 15 and 17 to their initial positions.

14. Record the compressive force.

15. Repeat steps 6 through 15 for several selected preset filing forces.

Figure 8:
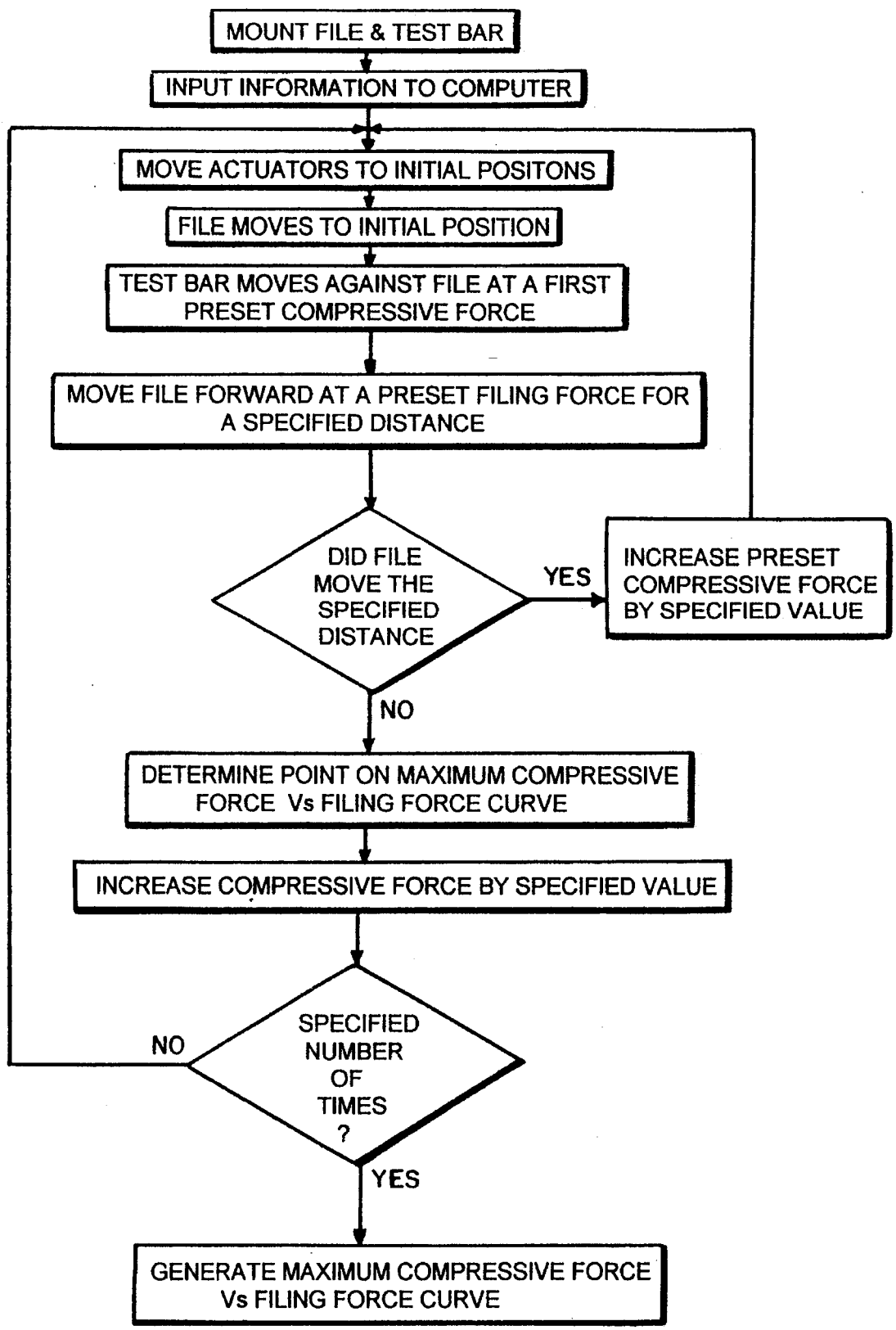
FIG. 8 shows a flow chart for implementing a test procedure to obtain a curve as depicted in FIG. 7.

Computer 21 can be programmed to implement such procedure in accordance with the flow chart depicted in FIG. 8.

The computer 21 can then generate a curve 31, such as shown in FIG. 7 from a determination of each successive maximum compressive force allowed at each preset filing force. Such curve can also be used as an indication of the relative sharpness characteristic of a file in a manner similar to that discussed with reference to FIG. 5. In this case a curve 31A, below curve 31, shows a file having a relatively high sharpness compared to that of curve 31, while a curve 31B, above curve 31, shows a file having a relatively low sharpness compared to that of curve 31. Again, the relative sharpness of a particular file can then be determined.

While the above process represents the preferred embodiment of the invention, modification thereto may occur to those in the art within the spirit and scope of the invention. Hence, the invention is not to be construed as limited to the specific embodiment described except as defined by the appended claims.

What is claimed is:

1. A method of testing a characteristic of a file comprising:

(a) moving a file for a selected number of strokes over the surface of a test bar of material for a preset distance at a selected filing force while maintaining a selected compressive force between the file and the test bar;

(b) measuring the amount of material that has been removed at the test bar surface at selected ones of said strokes during step (a);

(c) supplying the information obtained in step (b) to a computer and computing a partial curve of the amount of removed material as a function of the effective stroke area of the test bar over which the file has been moved during said selected number of strokes;

(d) calculating from said computed partial curve an overall curve which fits approximately an equation of the form $Y=A(1-e^{(-X/B)})$ where Y is the amount of removed material, X is the effective stroke area, and A and B are constants; and (e) selecting a specified value of the amount of removed material on the overall curve calculated in step (d) and determining the slope of a straight line from the origin of said overall curve to said specified value, said slope representing the cutting efficiency of the file being tested.

2. A method in accordance with claim 1 and further including:

(f) determining the value of the effective stroke area corresponding to the specified value of the amount of removed material, selected in step (e), the value of said effective stroke area representing the useful life of the file being tested.

3. A method in accordance with claims 1 or 2, wherein the specified value of the amount of removed material is a selected fraction of the maximum value thereof.

4. A method in accordance with claim 3, wherein the specified value is 95% of the maximum value of the amount of removed material thereof.

5. A method of testing a file comprising:

(a) mounting a file at an initial position on the surface of a test bar of material at a preset compressive force between the file and the test bar surface;

(b) moving the file over the test bar surface at a first selected filing force until the file stops;

(c) determining the position of the file when it stops and calculating the distance travelled from said initial position;

(d) repeating steps (b) and (c) for a successive number of times at successively increasing filing forces until the distance traveled is equal to a specified distance;

(e) recording a value of the minimum filing force needed to travel the specified distance;

(f) increasing the present compressive force by selected successive values and successively repeating steps (b), (c), (d), and (e) a selected number of times to record the minimum filing force needed at each successive value of the compressive force;

(g) determining a curve of minimum filing force as a function of the selected successive values of compressive force;

(h) performing steps (a) through (g) for a plurality of different files to be tested; and (i) comparing the relative values of the curves of minimum filing force values as a function of the selected successive values of compressive forces for said plurality of files to determine the relative sharpness characteristics of said plurality of files.

6. A method in accordance with claim 5, wherein the curves of said plurality of files in which the minimum filing force values are relatively higher compared to the minimum force values of the curves of others of said plurality of files are determined to have relatively higher sharpness characteristics.

7. A method of testing a file comprising:

(a) mounting a file at an initial position on the surface of a test bar of material at a first selected compressive force between the file and the test bar surface;

(b) moving the file over the test bar surface at a preset filing force and determining the distance the file moves over said test bar surface;

(c) increasing the compressive force by successively increasing values until the distance the file moves is less than a specified distance;

(d) recording the value of the maximum allowable compressive force that will not prevent the file from moving the specified distance;

(e) increasing the preset filing force by successively increasing values and repeating steps (b), (c), and (d) a selected number of times to record a maximum compressive force needed at each successive filing force value;

(f) determining a curve of maximum compressive force values as a function of the successive values of filing force;

(g) performing steps (a) through (f) for a plurality of different files to be tested; and (h) comparing the relative values of the curves of maximum compressive force values as a function of the successive values of filing force for said plurality of files to determine the relative sharpness characteristics of said plurality of files.

8. A method in accordance with claim 7, wherein the curves of said plurality of files in which the maximum compressive force values are relatively lower compared to the curves of maximum compressive force values of others of said plurality of files are determined to have relatively higher sharpness characteristics.

\* \* \* \* \*